United States Patent
Greenawalt

(10) Patent No.: US 10,890,574 B2
(45) Date of Patent: Jan. 12, 2021

(54) DIGESTION OF LEAD(0) AND SUBSEQUENT COLORIMETRIC DETECTION OF LEAD(II)

(71) Applicant: Hach Company, Loveland, CO (US)

(72) Inventor: Angella Nicholle Greenawalt, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 183 days.

(21) Appl. No.: 16/180,384

(22) Filed: Nov. 5, 2018

(65) Prior Publication Data

US 2020/0141916 A1    May 7, 2020

(51) Int. Cl.
| | |
|---|---|
| *G01N 21/78* | (2006.01) |
| *G01N 31/00* | (2006.01) |
| *G01N 31/22* | (2006.01) |
| *G01N 33/18* | (2006.01) |
| *G01N 33/20* | (2019.01) |

(52) U.S. Cl.
CPC ............. *G01N 33/18* (2013.01); *G01N 21/78* (2013.01); *G01N 31/005* (2013.01); *G01N 31/22* (2013.01); *G01N 33/20* (2013.01)

(58) Field of Classification Search
CPC ...... G01N 21/78; G01N 31/005; G01N 31/22; G01N 33/18; G01N 33/20; Y10T 436/17; Y10T 436/171538; Y10T 436/18; Y10T 436/182; Y10T 436/25125
USPC ..... 436/73, 77, 80, 106, 108, 119, 120, 164, 436/166, 175
See application file for complete search history.

(56) References Cited

U.S. PATENT DOCUMENTS

| | | | | |
|---|---|---|---|---|
| 8,133,739 | B2 * | 3/2012 | Asano | G01N 31/22 436/164 |
| 2002/0187558 | A1 * | 12/2002 | Bodkin | G01N 33/1813 436/164 |
| 2011/0020943 | A1 * | 1/2011 | Okamoto | G01N 21/78 436/73 |
| 2017/0097300 | A1 * | 4/2017 | Lu | G01N 21/78 |
| 2020/0057042 | A1 * | 2/2020 | Hill | H04N 1/56 |

OTHER PUBLICATIONS

Klinnant et al. Mikrochim. Acta, vol. 108, 1992, pp. 11-17.*

* cited by examiner

*Primary Examiner* — Maureen Wallenhorst
(74) *Attorney, Agent, or Firm* — Ference & Associates LLC

(57) ABSTRACT

An embodiment provides a method for measuring a concentration of lead(0) in an aqueous sample, including: introducing an aqueous sample to a reaction vessel; adding a copper(II) acetate material to the aqueous sample in the reaction vessel; chelating unreacted copper(II) material by introduction of an organosulfur compound to the aqueous sample in the reaction vessel; adding a colorimetric indicator to the aqueous sample in the reaction vessel; and measuring a concentration of lead(II) in the aqueous sample by measuring a colorimetric change of the aqueous sample caused by a reaction of lead(II) within the aqueous sample with the colorimetric indicator. Other aspects are described and claimed.

18 Claims, 3 Drawing Sheets

DIGESTION OF LEAD(0) AND SUBSEQUENT COLORIMETRIC DETECTION OF LEAD(II)

FIELD

This application relates generally to water quality testing, and, more particularly, to digestion and measurement of lead(0) in an aqueous sample.

BACKGROUND

Measurement of lead is important to ensure water quality. Lead is a toxic metal which may be harmful to humans and animals even at low levels. Constant lead exposure may cause lead levels to accumulate in an animal, thereby causing physical damage to the animal over time. Fetuses, infants, and young children, are the most affected by physical and behavioral damage from lead since even very low doses of lead accumulate in younger bodies. Lead exposure may cause permanent mental and physical developmental abnormalities. Lead may damage the central and peripheral nervous system. Cognitive, behavioral, and physical deficits may occur, for example, learning disabilities, stunted growth, hearing impairment, blood diseases, stupor, coma, loss of kidney function, and brain damage. Proper detection and mitigation of lead levels is critical for water treatment, natural bodies of water, food manufacturing, pharmaceuticals, and manufacturing processes.

BRIEF SUMMARY

In summary, one embodiment provides a method for measuring a concentration of lead(0) in an aqueous sample, comprising: introducing an aqueous sample to a reaction vessel; adding a copper(II) acetate material to the aqueous sample in the reaction vessel; chelating unreacted copper(II) material by introduction of an organosulfur compound to the aqueous sample in the reaction vessel; adding a colorimetric indicator to the aqueous sample in the reaction vessel; and measuring a concentration of lead(II) in the aqueous sample by measuring a colorimetric change of the aqueous sample caused by a reaction of lead(II) within the aqueous sample with the colorimetric indicator.

Another embodiment provides a device for measuring a concentration of lead(0) in an aqueous sample, comprising: a processor; a memory device that stores instructions executable by the processor to: introduce an aqueous sample to a reaction vessel; add a copper(II) acetate material to the aqueous sample in the reaction vessel; chelate unreacted copper(II) material by introduction of an organosulfur compound to the aqueous sample in the reaction vessel; add a colorimetric indicator to the aqueous sample in the reaction vessel; and measure a concentration of lead(II) in the aqueous sample by measuring a colorimetric change of the aqueous sample caused by a reaction of lead(II) within the aqueous sample with the colorimetric indicator.

A further embodiment provides a method for digesting lead(0) in an aqueous solution, comprising: introducing an aqueous sample to a reaction vessel; adding a copper(II) acetate material to the aqueous sample in the reaction vessel; chelating unreacted copper(II) material by introduction of a thiourea to the aqueous sample in the reaction vessel; adding a colorimetric indicator comprising xylenol orange tetrasodium salt to the aqueous sample in the reaction vessel; and measuring a concentration of lead(II) in the aqueous sample by measuring a colorimetric change of the aqueous sample caused by a reaction of lead(II) within the aqueous sample with the colorimetric indicator.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
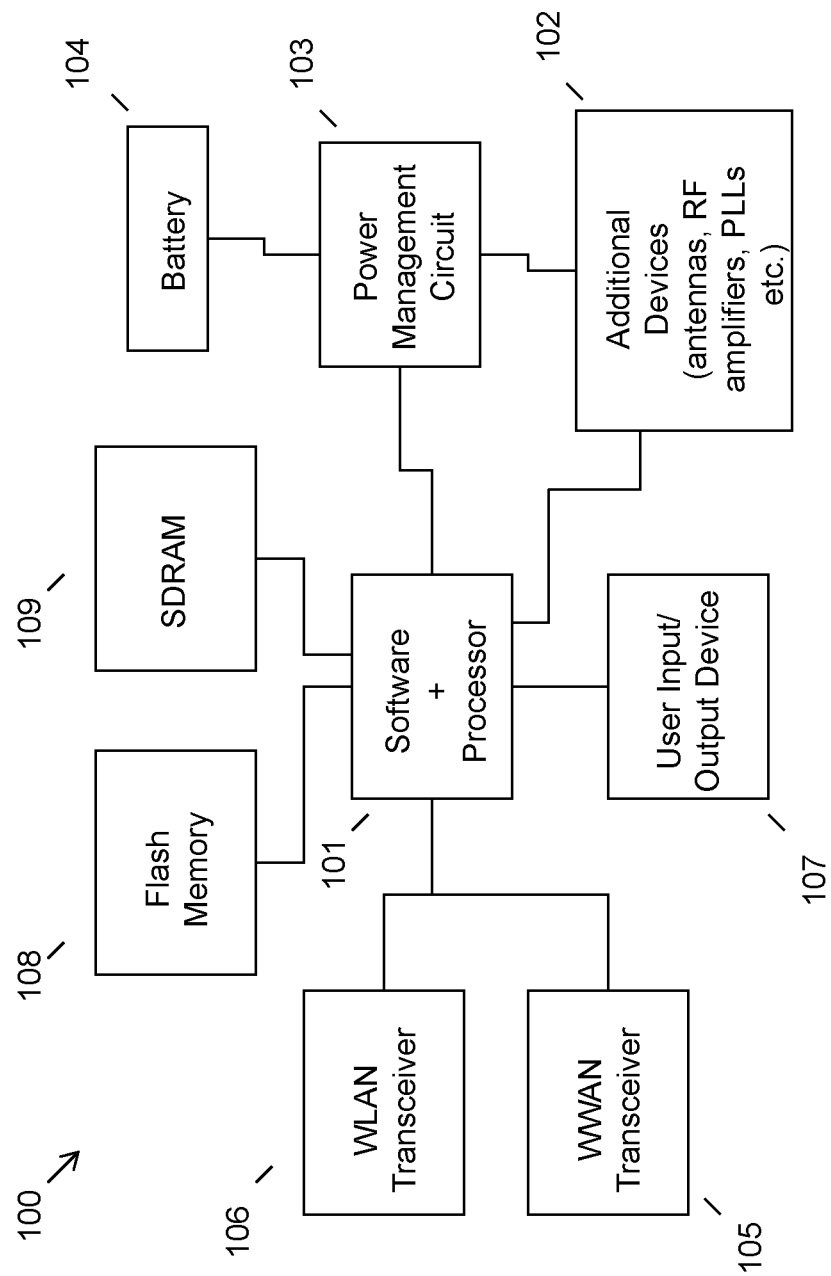
FIG. 1 illustrates an example of computer circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Lead exposure remains an environmental and health issue around the world. Young children, infants, and fetuses are most vulnerable to lead. The youngest members of the population are most vulnerable because lower exposure levels may cause physical and behavioral effects as compared to adults. Lead exposure in children has been linked to central and peripheral nervous system damage, learning disabilities, shorter stature, impaired hearing, lower IQ, hyperactivity, and impaired formation and function of blood cells. Lead may accumulate in a body over time where it may be stored in tissue including bone. During pregnancy lead may be transferred to the fetus since lead may travel across the placental barrier. This may result in reduced growth of the fetus and premature birth. The United States Environmental Protection Agency and other country's counterparts have set acceptable lead exposure levels. However, in order to know if the exposure is within acceptable limits, the amount of lead present in a substance must be measured. A common method of lead ingestion is through drinking water. However, other sources such as paint, dust, soil, and food may also contain lead.

Lead may be present in water through many sources. For example, lead may be naturally occurring or introduced by industrial waste or the like. Another lead contributor may be service line infrastructure such as lead pipes. Water with a high acidity or low mineral content may corrode lead pipes at a faster rate. Also, water that sits in a lead vessel or pipes may also contain lead. Factors that may affect how much lead from supply infrastructure includes the chemistry of the water, mineral level, lead content of the piping, wear of piping, time of water in a lead pipe, or the like. Whatever the source of the lead, the proper measurement and detection of lead is critical to communities, municipalities, facilities, or the like.

However, traditional methods of measuring lead may have some limitations. It may be possible to analyze potable water for lead using ammoniacal citrate-cyanide reducing solution. This may be followed by extraction with dithizone in chloroform. The final solution may then be analyzed photometrically. However, this method may not be reliable for detecting low levels of lead in water. Additionally, the use of solvents and cyanide necessary for measuring the lead may present a disposal problem. Therefore, this method is not readily useful except in a laboratory environment in which reagent volumes may be kept to a minimum and test reagents may be captured for proper disposal.

Another lead detection method may use special ion exchange resins. This method may require carefully controlled flow rates for passing fluid solutions through the material in order to retain the metals on the resins. Such materials may be of a small particle size. Additionally, the flow rates may be extremely slow making the analysis very time consuming. Also, the required elution step may involve the use of strong acids or specific flow rates to separate the metals. Therefore, ion exchange resins may have some limitations.

Accordingly, the systems and methods described herein provide a technique for measuring the concentration of lead in an aqueous sample. Specifically, the systems and methods as described herein may digest lead(0) to lead(II). The lead(0) may be digested using copper(II) acetate material. In an embodiment, the lead may be measured by colorimetry. The colorimetric measurement may be made using an indicator. The indicator may be sensitive to lead(II). The system and method described herein may measure a concentration of lead(II) using a colorimetric technique. The colorimetric measurement may be performed by an automated machine capable of measuring absorbance, or by visual means. Thus, the described technique provides a method for measuring lead that does not require hazardous materials that are difficult to dispose of and also provides a method where the measurement can occur in a typical measurement system.

The illustrated example embodiments will be best understood by reference to the figures. The following description is intended only by way of example, and simply illustrates certain example embodiments.

While various other circuits, circuitry or components may be utilized in information handling devices, with regard to an instrument for lead measurement according to any one of the various embodiments described herein, an example is illustrated in FIG. 1. For example, the device circuitry as described in FIG. 1 may be used for communicating measurements to another device or may be used as the device for receiving measurements. Device circuitry 100 may include a measurement system on a chip design found, for example, a particular computing platform (e.g., mobile computing, desktop computing, etc.) Software and processor(s) are combined in a single chip 101. Processors comprise internal arithmetic units, registers, cache memory, busses, I/O ports, etc., as is well known in the art. Internal busses and the like depend on different vendors, but essentially all the peripheral devices (102) may attach to a single chip 101. The circuitry 100 combines the processor, memory control, and I/O controller hub all into a single chip 101. Also, systems 100 of this type do not typically use SATA or PCI or LPC. Common interfaces, for example, include SDIO and I2C.

There are power management chip(s) 103, e.g., a battery management unit, BMU, which manage power as supplied, for example, via a rechargeable battery 104, which may be recharged by a connection to a power source (not shown). In at least one design, a single chip, such as 101, is used to supply BIOS like functionality and DRAM memory.

System 100 typically includes one or more of a WWAN transceiver 105 and a WLAN transceiver 106 for connecting to various networks, such as telecommunications networks and wireless Internet devices, e.g., access points. Additionally, devices 102 are commonly included, e.g., a transmit and receive antenna, oscillators, RF amplifiers, PLLs, etc. System 100 includes input/output devices 107 for data input and display/rendering (e.g., a computing location located away from the single beam system that is easily accessible by a user). System 100 also typically includes various memory devices, for example flash memory 108 and SDRAM 109.

It can be appreciated from the foregoing that electronic components of one or more systems or devices may include, but are not limited to, at least one processing unit, a memory, and a communication bus or communication means that couples various components including the memory to the processing unit(s). A system or device may include or have access to a variety of device readable media. System memory may include device readable storage media in the form of volatile and/or nonvolatile memory such as read only memory (ROM) and/or random access memory (RAM). By way of example, and not limitation, system memory may also include an operating system, application programs, other program modules, and program data. The disclosed system may be used in an embodiment to perform lead measurement of an aqueous sample.

Figure 2:
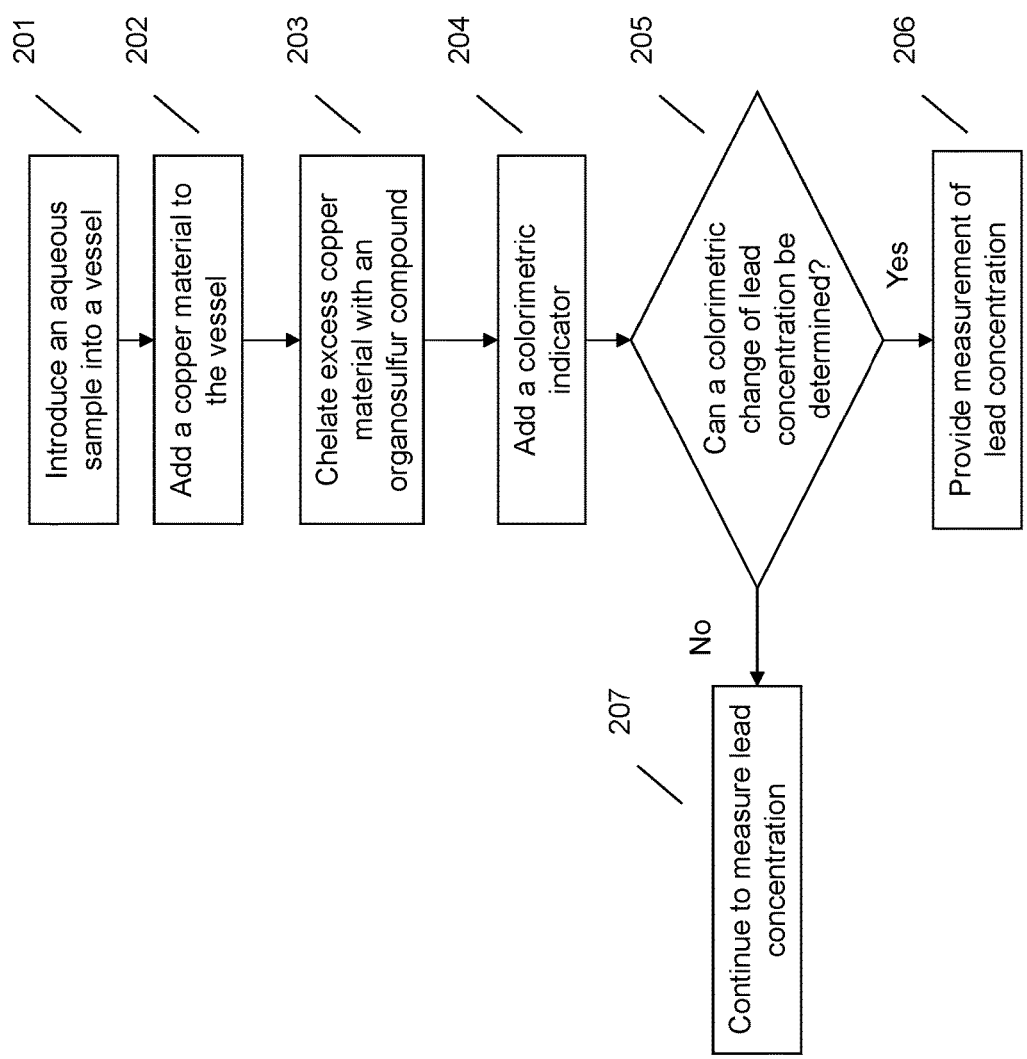
FIG. 2 illustrates a flow diagram of an example lead digestion and measuring system.

Referring now to FIG. 2, an embodiment may digest lead(0) in a sample to a lead(II) form, thereby allowing measurement of the lead in the sample. The lead(II) may be measured using a colorimetric indicator. The digestion of lead(0) to lead(II) may be facilitated using a copper(II) acetate material. In an embodiment, unreacted copper(II) may be chelated. The chelation may be performed using an organosulfur compound. In an embodiment, the lead(II) may be measure using a colorimetric indicator. Colorimetric measurement may be performed using a laboratory apparatus or a visual method.

At 201, in an embodiment, a sample may be introduced into a vessel. The sample may contain lead. The lead may be in a solid or an aqueous form. For example, the lead may be a solid wire, particle, suspension, or the like. Additionally or alternatively, the lead may be in a liquid form or a finely suspended form in the aqueous sample. In an embodiment, the lead sample may be added to a reaction vessel. The introduction of the lead sample may be automated or manual. For example, a sample for testing may be pumped, aliquoted, pipetted, or introduced in any manner into a vessel. The lead for testing may be from any number of sources, for example, the lead may be from municipal water, industrial effluent, a natural waterway, a manufacturing process, or the like. The method and system may have more than one reaction vessel. For example, a lead sample may be introduced into a first vessel and subsequent steps of an embodiment may occur in another vessel or vessels.

The aqueous sample may include a sample from a natural body of water, a holding tank, a processing tank, a pipe, or the like. The lead containing sample may be in a continuous flow, a standing volume of liquid, or any combination thereof. In one embodiment, the lead containing sample may be introduced to a vessel, for example, a test chamber of the measurement device. Introduction of the lead containing sample into the measurement device may include placing or introducing the lead containing sample into a test chamber manually by a user or using a mechanical means, for example, gravity flow, a pump, pressure, fluid flow, or the like. For example, a water sample for lead testing may be introduced to a measurement or test chamber using a pump. In an embodiment, valves or the like may control the influx and efflux of the aqueous solution into or out of the one or more chambers, if present. Additionally or alternatively, the measurement device may be present within or introduced into a volume of the lead containing sample. The measurement device is then exposed to the volume of aqueous sample where it can perform measurements. The system may be a flow-through system in which a lead containing sample and/or reagents are automatically mixed and measured. Once the sample is in contact with the measurement system, the system may measure the lead in the sample using colorimetric techniques. In an embodiment, the measurement device may include one or more chambers in which the one or more method steps may be performed.

Figure 3:
FIG. 3 illustrates a chemical equation of an example of lead(0) digestion and subsequent lead(II) detection.
Figure 3:
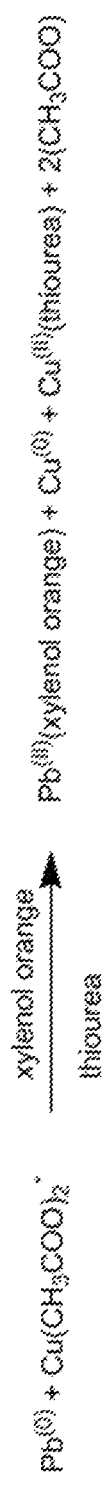

At 202, in an embodiment, the lead may be oxidized. Specifically, the lead(0) sample may be oxidized to lead(II). The lead oxidation may be facilitated using a copper(II) acetate material that is introduced into the reaction vessel, either manually or automatically, for example, using one of the methods as described above with respect to introduction of the aqueous sample to the reaction vessel. The copper material may be a copper(II) cation. In an embodiment, the lead may displace copper(II) from copper(II) acetate to generate lead(II) in the solution. Lead(II) can be colorimetrically measured, as described in more detail herein. An example embodiment of lead(0) digestion is illustrated in FIG. 3. In an embodiment, the pH of the digestion may be monitored and controlled to facilitate lead(0) digestion.

At 203, in an embodiment, the system may chelate unreacted copper(II) material from the solution to prevent interference with a colorimetric indicator. Thus, in an embodiment, a copper(II) scavenger may be added to chelate any unreacted copper(II) material. In an embodiment, chelation may be performed by an organosulfur compound, for example, thiourea. For example, unreacted copper(II) may be chelated using thiourea. The chelating agent such as an organosulfur compound may be automatically or manually added to a vessel. A chelation step may be performed in the same vessel as other steps in the method, or in different vessel. For example, for proper pH control and/or separation of solids from liquids, the steps may be performed in different vessels or the same vessel. A system of piping, valves, screen, filters, or the like may facilitate the digestion of lead(0) and measurement of lead(II).

At 204, in an embodiment, the method and system may use a colorimetric indicator. The colorimetric indicator may be sensitive to lead(II) and may therefore react with lead(II) in the solution to create a colorimetric change in the solution. The colorimetric indicator may be water soluble. The colorimetric indicator may be xylenol orange tetrasodium salt. The indicator may give a visual indication of lead(II) concentration, which may be determined via absorbance measurements made using a laboratory apparatus. The resulting color or absorbance from the indicator with the lead(II) in the sample may be determined photometrically, for example, using a spectrophotometer.

The concentration of lead(II) may be determined in many ways. For example, comparison of a known concentration of lead(II) with the indicator may be used to create a calibration curve of known lead(II) concentrations. As another example, the absorbance of a sample containing lead(II) may be determined using a set of known concentration lead(II) samples to generate a calibration curve.

At 205, the system may determine whether a colorimetric change occurred within the solution. Specifically, a colorimetric change may occur in the solution due to the existence of a lead(II) concentration in the solution. For example, lower concentrations of lead(II) may yield a yellow colored solution and higher concentrations of lead(II) may yield a pink colored solution. Colors are illustrative and may be different based upon the indicator used. Other indicators and colors are contemplated and disclosed. Additionally or alternatively, the method and system may use an absorbance measuring device to measure the lead(II) indicator complex absorbance. For example, the delta absorbance may increase as the concentration of the lead(II) increases in a sample. Colorimetric measurement may be performed with standard laboratory equipment such as a spectrophotometer.

The determination may also be made based upon a predicted absorbance under known conditions. Predictions may be based upon variables such as temperature, pH, turbidity, chelation, scavenging, or the like. For example, the system may be programmed with a calibration curve. Deviations from the predicted curve may make results less reliable and cause the system to discontinue measuring or to send an alert. As another example, the system may receive information indicating a number of measurement cycles measuring lead(II) concentration are outside acceptable limits. For example, such measurements may indicate that a step in the process may be suboptimal. Such steps may include lead digestion, chelating, scavenging, indicator concentration, pH, temperature, or the like. At 207, in an embodiment, if a concentration of lead(II) cannot be determined, the system may continue to measure lead(II), obtain another sample, attempt to digest lead(0) to lead(II), add copper chelator, or the like. Additionally or alternatively, the system may output an alarm, log an event, or the like.

At 206, in an embodiment, if a colorimetric change is determined, detected, or identified, the system may provide a measurement of lead(II) concentration. This measurement may then be correlated to a concentration of lead within the aqueous sample, thereby providing a measurement of the lead within the aqueous sample. The measurement system may connect to a communication network, for example, using a wireless communication connection, a wired communication connection, through another device, or the like. Through this communication network, the system may alert a user or a network. This alert may occur whether a lead(II) measurement is determined or not. An alert may be in a form of audio, visual, data, storing the data to a memory device, sending the output through a connected or wireless system, printing the output or the like. The system may log information such as the measurement value, measurement location, a corrective action, geographical location, time, date, number of measurement cycles, or the like. The alert or log may be automated, meaning the system may automatically output whether a correction was required or not. The system may also have associated alarms, limits, or predetermined thresholds. For example, if a lead(II) concentration reaches a threshold. Alarms or logs may be analyzed in real-time, stored for later use, or any combination thereof.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device, where the instructions are executed by a processor. In the context of this document, a storage device is not a signal and "non-transitory" includes all media except signal media.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and products according to various example embodiments. It will be understood that the actions and functionality may be implemented at least in part by program instructions. These program instructions may be provided to a processor of a device, e.g., a hand held measurement device such as illustrated in FIG. 1, or other programmable data processing device to produce a machine, such that the instructions, which execute via a processor of the device, implement the functions/acts specified.

It is noted that the values provided herein are to be construed to include equivalent values as indicated by use of the term "about." The equivalent values will be evident to those having ordinary skill in the art, but at the least include values obtained by ordinary rounding of the last significant digit.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method for measuring a concentration of lead(0) in an aqueous sample, comprising:
    introducing an aqueous sample to a reaction vessel;
    adding a copper(II) acetate material to the aqueous sample in the reaction vessel, wherein lead(0) within the aqueous sample reacts with the copper(II) acetate material to generate lead(II);
    chelating unreacted copper(II) acetate material by introduction of an organosulfur compound to the aqueous sample in the reaction vessel;
    adding a colorimetric indicator to the aqueous sample in the reaction vessel;
    measuring a concentration of lead(II) in the aqueous sample by measuring a colorimetric change of the aqueous sample caused by a reaction of lead(II) within the aqueous sample with the colorimetric indicator; and
    correlating the measurement of the concentration of lead (II) in the aqueous sample to the concentration of lead(0) in the aqueous sample.

2. The method of claim 1, wherein the aqueous sample is maintained at a predetermined pH value.

3. The method of claim 1, wherein the measuring a concentration of lead(II) comprises measuring the generated lead(II).

4. The method of claim 1, wherein the measuring comprises measuring an absorbance at a wavelength based upon the lead(II) concentration.

5. The method of claim 4, wherein the measuring further comprising calculating a change of absorbance based upon the lead(II) concentration.

6. The method of claim 1, wherein the copper(II) acetate material generates a cupric cation.

7. The method of claim 1, wherein the organosulfur compound is thiourea.

8. The method of claim 1, wherein the indicator is xylenol orange tetrasodium salt.

9. The method of claim 1, wherein the indicator is a water soluble species.

10. A device for measuring a concentration of lead(0) in an aqueous sample, comprising:
    a reaction vessel; a means for introducing an aqueous sample, a copper(II) acetate material, an organosulfur compound, and a colorimetric indicator into the reaction vessel
    a processor;
    and a memory device that stores instructions executable by the processor to:
    introduce the aqueous sample to the reaction vessel;
    add the copper(II) acetate material to the aqueous sample in the reaction vessel, wherein lead(0) within the aqueous sample reacts with the copper(II) acetate material to generate lead(II);
    chelate unreacted copper(II) acetate material by introduction of the organosulfur compound to the aqueous sample in the reaction vessel;
    add the colorimetric indicator to the aqueous sample in the reaction vessel;
    measure a concentration of lead(II) in the aqueous sample by measuring a colorimetric change of the aqueous sample caused by a reaction of lead(II) within the aqueous sample with the colorimetric indicator; and correlate the measurement of the concentration of lead(II) in the aqueous sample to the concentration of lead(0) in the aqueous sample.

11. The device of claim 10, wherein the aqueous sample is maintained at a predetermined pH value.

12. The device of claim 10, wherein the measuring a concentration of lead(II) comprises measuring the generated lead(II).

13. The device of claim 10, wherein the measuring comprises measuring an absorbance at a wavelength based upon the lead(II) concentration.

14. The device of claim 13, wherein the measuring further comprising calculating a change of absorbance based upon the lead(II) concentration.

15. The device of claim 10, wherein the copper(II) acetate material generates a cupric cation.

16. The device of claim 10, wherein the organosulfur compound is thiourea.

17. The device of claim 10, wherein the indicator is xylenol orange tetrasodium salt.

18. A method for measuring a concentration of lead(0) in an aqueous sample, comprising:
   introducing an aqueous sample to a reaction vessel;
   adding a copper(II) acetate material to the aqueous sample in the reaction vessel, wherein lead(0) within the aqueous sample is digested to lead(II) by reaction with the copper(II) acetate material;
   chelating unreacted copper(II) acetate material by introduction of a thiourea to the aqueous sample in the reaction vessel;
   adding a colorimetric indicator comprising xylenol orange tetrasodium salt to the aqueous sample in the reaction vessel;
   measuring a concentration of lead(II) in the aqueous sample by measuring a colorimetric change of the aqueous sample caused by a reaction of lead(II) within the aqueous sample with the colorimetric indicator; and
   correlating the measurement of the concentration of lead (II) in the aqueous sample to the concentration of lead(0) in the aqueous sample.

\* \* \* \* \*